United States Patent [19]

Dubois et al.

[11] 4,085,443

[45] Apr. 18, 1978

[54] KEYBOARD OPERATED APPARATUS FOR SIMULTANEOUS CODING AND DISPLAY OF CHEMICAL STRUCTURE AND SIMILAR GRAPHICAL INFORMATION

[75] Inventors: Jacques E. Dubois; John A. Miller, both of Paris, France

[73] Assignee: Agence Nationale de Valorisation de la Recherche, Neuilly-sur-Seine, France

[21] Appl. No.: 611,197

[22] Filed: Sep. 8, 1975

[30] Foreign Application Priority Data

Sep. 16, 1974   France .................................. 74 31244

[51] Int. Cl.² .......................... G06F 3/14; G06F 3/06; G06F 3/02
[52] U.S. Cl. ................................ 364/900; 340/324 A
[58] Field of Search ............ 340/172.5, 324 R, 324 A, 340/324 AD, 336, 365 R; 35/6, 9 A, 9 R, 18 R, 18 A; 364/900

[56] References Cited

U.S. PATENT DOCUMENTS

| | | | |
|---|---|---|---|
| 3,325,914 | 6/1967 | Bliss et al. | 35/18 R |
| 3,368,290 | 2/1968 | Loeb | 340/336 X |
| 3,534,338 | 10/1970 | Christensen et al. | 340/172.5 |
| 3,681,646 | 8/1972 | Brehm | 340/324 A X |
| 3,731,299 | 5/1973 | Bouchard et al. | 340/324 A |
| 3,750,135 | 7/1973 | Carey et al. | 340/324 AD |
| 3,787,988 | 1/1974 | Nakajima et al. | 35/6 X |
| 3,811,113 | 5/1974 | Saito et al. | 340/172.5 |

Primary Examiner—Melvin B. Chapnick
Attorney, Agent, or Firm—Flynn & Frishauf

[57] ABSTRACT

Graphical information, such as a structural chemical formulae, composed of nodes and links between the nodes, or in a chemical formula ring positions and bonds, are coded by means of logic circuits responsive to actuation of a keyboard. The graphical data coded in binary digit form are stored, while contents of the store are scanned, decoded and applied in analog form to a display device. When recorded on a suitable medium they are made machine readable, for searching or similar processing. A luminous cursor indicates on the display the part of a structural formula that is subject to the next keyboard action. The store is organized about fixed display locations available as nodes. Alphanumeric characters identify atoms at nodes. Single, double or triple bonds in any of eight directions from a node towards another node may be registered and displayed. A cursor address register, a store address register and a comparator are used. Registering at one node a bond designated by character and direction transfers the cursor to the node at the other end of the designated bond. Other transfers of the cursor may be effected by the space bar with the use of the appropriate directional keyed instruction.

7 Claims, 4 Drawing Figures

KEYBOARD OPERATED APPARATUS FOR SIMULTANEOUS CODING AND DISPLAY OF CHEMICAL STRUCTURE AND SIMILAR GRAPHICAL INFORMATION

BACKGROUND OF THE INVENTION

The present invention relates to an apparatus for the coding or display, or simultaneous coding and display, of graphical information, more particularly of graphical data composed of nodes and links between these nodes, each node being capable of identification by at least one alphanumeric character and each link being capable of identification by its nature and its direction.

Apparatus of this type is already known for coding and simultaneous display of chemical formulae of the structural type. Because of the extremely high number of identified chemical compounds, it has been found necessary to undertake systematic recording of their formulae in coded form. The coded formula is transcribed on a record medium, such as a perforated card, perforated tape or magnetic tape, compatible with a data processing installation in order to permit later exploitation of the recorded formulae by computer, especially for documentary research operations. It is essential to check visually the accuracy of the coded formula and, preferably the coding and display of the formula take place simultaneously. Two types of apparatus are at present used for this purpose.

Apparatus of the first type comprises special typewriting machines with which a structural chemical formula to be coded is simultaneously reproduced on a paper sheet and on a magnetic tape or perforated tape. The printed result on the sheet allows visual verification and the magnetic tape or perforated tape is later read by a computer and the recorded data are used as a basis for the elaboration of the code. The keyboard of these typewriting machines comprises all the keys necessary for the reproduction of the particular symbols of these chemical formulae; in particular, the bonds are represented by vertical, horizontal or oblique dashes. In addition, the elementary operations such as spacing, return, line spacing which, although effected on the keyboard do not result in a print on paper, are recorded on the magnetic tape or perforated tape. Such apparatus has many disadvantages; in particular, errors which occur when the formula is typed cannot be corrected, the positioning of the carriage and the roller require relatively long mechanical displacements and the recording on magnetic tape or perforated tape must be processed by computer to permit its later exploitation in an information centre.

Apparatus of the second type requires a computer coupled on the one hand to a special keyboard similar to that of apparatus of the first type, and on the other hand to a cathode ray system for the display. Utilisation of this type of installation requires the preparation of a special program which first interprets the operation at the keyboard and then derives the elements to be coded and the image to be displayed. In addition to the high cost of their use, such installations require too long a processing time for the data to permit a sufficiently rapid scanning of the cathode ray tube screen to permit the provision on the screen of an image acceptable and not troublesome to an operator at the visual level. Although this would complicate the installation even more, one might thus be led to provide an intermediate data record medium, such as a video tape or disc on which the graphic data is recorded in analogue form, which data may then be displayed on the screen by reading this record medium.

BRIEF SUMMARY OF THE INVENTION

The invention has for its object to provide an apparatus which overcomes the above-mentioned disadvantages of the known apparatus.

In more general terms, the invention has for its object to provide an apparatus whose logic is at least partly wired and which permits simultaneous coding and display of data in graphical form, and also permits the provision of a recording of the coded graphical data and alphanumeric data which may be associated with it, which is directly usable by a computer.

The present invention also has for its object to provide an apparatus which operates in autonomous fashion, in particular an apparatus which does not require for coding and display the use of a computer programmed for this purpose.

This object is attained by an apparatus having logic that is at least partly wired in for coding, or display of graphic data such as a chemical formula in structural form. Wired logic can advantageously be used both for coding and display, preferably for simultaneous coding and display. Structural chemical formulae can be broken down into nodes or ring positions and links or bonds between these positions, a node or ring position being identifiable by at least one alpha-numeric character and a link or bond being identifiable by its nature and its direction, the said apparatus comprising a keyboard on which are provided a first assembly of keys carrying alphanumeric characters, a second assembly of keys carrying signs defining the different natures and directions of links and a third assembly of keys for control purposes. A coding circuit is linked to the keyboard to code the data appearing on the keys when these latter are operated. In accordance with the invention, the apparatus also comprises a store of the erasable kind in which graphic data coded in a manner identifying the nodes or ring positions and links are introduced in numerical form, a circuit scanning the contents of the store and a decoding circuit for decoding the stored data and transmitting them in analogue form to a display device, comprising a screen on which appears, in graphical form, at least a part of the whole of the stored data. There is thus direct correspondence between the data introduced by the operator, that which is contained in the store, and that which is displayed.

According to a preferred feature of the invention, the store comprises a fixed number of locations and the screen comprises a fixed number of points at most equal to the number of store locations; the coded data relating to a node, that is to say the data defining each node or ring position and the links which extend from it, is stored in different store locations and the node positions of the graphical display on the screen coincide with the locations of the points on the screen, the group of points on the screen constituting at least a part of the image-like representation of the group of store locations.

According to another preferred feature of the invention, the coding circuit comprises:

means for positioning a cursor or index, preferably of high luminosity, at a point on the screen following operation of control keys on the keyboard, a cursor address register, the input of which is connected to the keyboard and the contents of which represent the position of the cursor on the screen, a store address register, the input of which is connected to the scanning circuit and the contents of which are continually varied to effect a scanning of all locations of the store and a comparator circuit, the inputs of which are connected to the outputs of the cursor address and store address registers and which provides at its output a signal to authorise the storing of graphical data relating to a node, the position of which corresponds to that of the cursor on the screen when the contents of the cursor address and memory address registers are identical.

Advantageously, a device for recording directly on to a record medium capable of use by a computer is linked to the store to record the stored coded data.

Other features and advantages of the invention will become apparent from the particular form of construction of the invention hereinafter described, by way of non-limiting example, with reference to the figures of the accompanying drawings, in which:

DESCRIPTION OF THE PREFERRED EMBODIMENT

Figure 1:
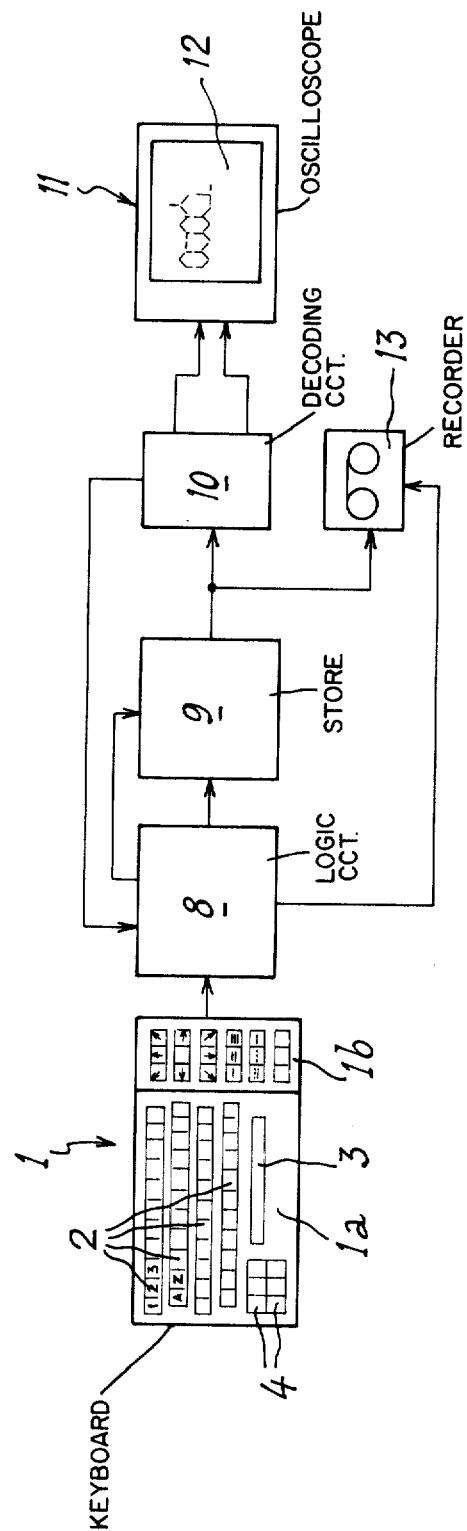
FIG. 1 is a functional diagram of an apparatus embodying the invention.

FIG. 1 is an overall functional diagram of an apparatus for the coding and displaying of structural chemical formulae. In their structural form, chemical formulae are represented in a graphical form comprising nodes or ring positions and links or bonds between these nodes or ring positions. A node or ring position is characterised by the chemical symbol of the element which is located at that node or ring position and this symbol is represented by characters of alphanumeric type. In the following, we mean by "alphanumeric characterized" the letters, numerals, signs *, +, −, and other ideograms. Each link or bond is characterised by its nature and its direction. Bonds are of various natures: single bond, double bond or triple bond, bonds shown in full lines and bonds shown in any other desired fashion, usually by a series of aligned points or two such series disposed parallel to one another or by a series of dashes. Finally, a bond may have eight possible directions with respect to a node or position, according to a known simplified mode of representation. The apparatus described hereinafter permits a coding and graphical display for which each node or ring position is characterised by three alphanumeric characters at most and the number of bonds extending from a single node or ring position is at most equal to three.

Figure 3:
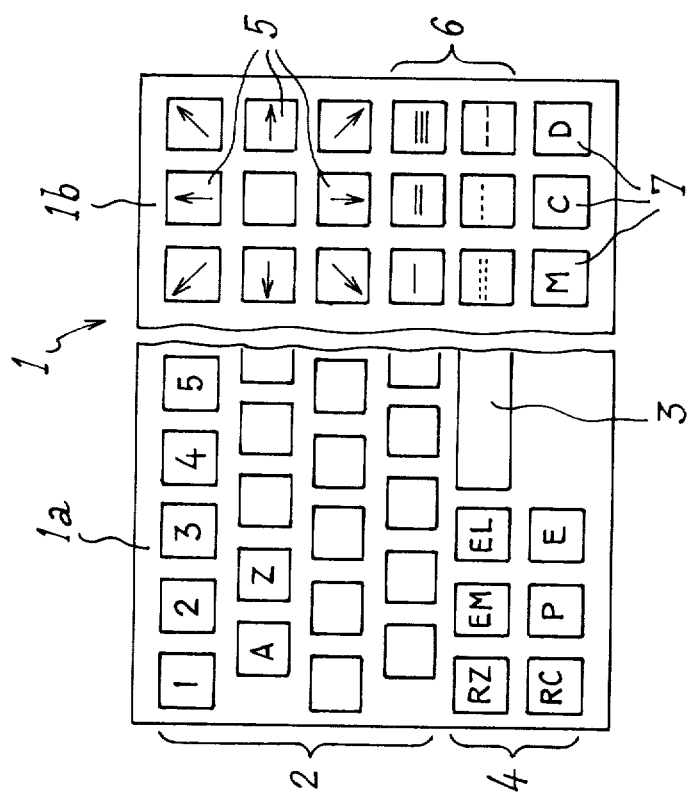
FIG. 3 shows diagrammatically the keyboard of the apparatus of FIG. 1.

The apparatus, of which the overall diagram is shown in FIG. 1, comprises a keyboard 1 (FIGS. 1 and 3) divided into a main keyboard 1a and an auxiliary keyboard 1b. The main keyboard 1a comprises the alphanumeric keys 5 and the space bar 3 of a standard typewriter keyboard as well as control keys 4 the functions of which will be explained later. The auxiliary keyboard 1b comprises eight keys 5 representing the directions of the bonds, six keys 6 representing the nature of the bonds and three control keys 7 the functions of which will be explained later.

The keyboard 1 is linked to a logic circuit 8 which interprets and codes the graphical data, that is to say the data relating to the nodes or positions and the bonds, and the control data, which comes from the keyboard 1. The logic circuit 8 additionally controls the storing of the coded graphical data in the store 9, as well as the display of this data. The coded graphical data is decoded by a decoding circuit 10 the output of which is connected to a display device, such as a cathode ray oscilloscope 11 on the screen 12 of which is displayed the stored coded formula.

Figure 4:
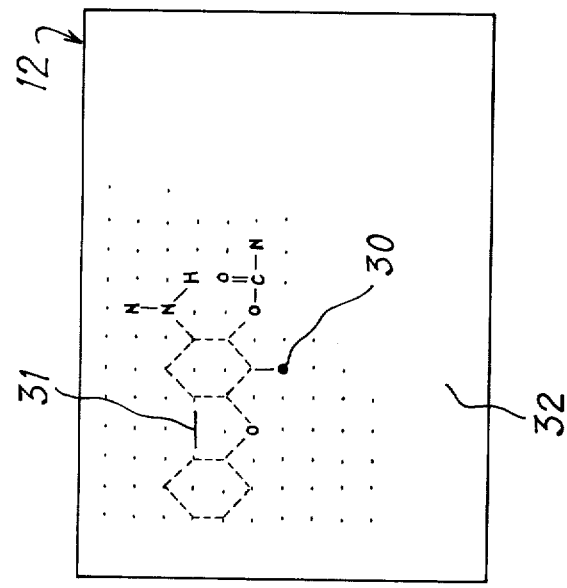
FIG. 4 is a diagrammatic representation of a formula displayed on the screen of the apparatus of FIG. 1.

The storing of this formula is carried out by successively addressing to different locations of the store 9, graphical data relating to the nodes or ring positions, that is to say data characterizing each node or ring position and the bonds which extend from it. The display of the formula is carried out on the screen 12 by positioning the nodes of the graphical outlines at the locations of points appearing on the screen. The screen 12 of the cathode ray oscilloscope 11 comprises 160 points which are displayed with a low luminosity (FIG. 4). An index or cursor 30 is displayed on the screen with a high luminosity and indicates to the operator the working position of the keyboard at a given moment. The cursor 30 is automatically displaced after the storing of data representing a bond and moves to the end of this bond; it can also be positioned at any point whatever on the screen by successive operations of a direction key 5 and of the space bar 3.

In the example shown in FIG. 4, the screen 12 comprises only 160 points and this number of points may not be sufficient to display the whole of the formula. In fact, the store 9 comprises a number of store locations greater than the number of points on the screen 12. By operation of a direction key 5 and the control key D of the auxiliary keyboard 1b, it is possible to displace the image on the screen in the selected direction with respect to the image-like representation of the store 9 and thus to explore the whole of the store locations.

The control of the store and of the display is effected by the logic circuit 8 which comprises a circuit for scanning the total contents of the store. This scanning is effected at a frequency greater than 15 Hz to avoid subjecting the operator to visual discomfort; for example, it may be equal to half the mains frequency (25 Hz in Europe), which permits a good image to be obtained on the screen 12. Generally, the selected frequency will be as high as possible compatible with the operating times of the circuits utilised.

Finally, the coded and stored formula can be recorded on a record medium, such as a magnetic tape or a perforated strip by means of a recorder 13 the input of which is connected to the output of the store 9. The control key P (strip perforation) or E (magnetic recording) of the principal keyboard 1a is responsible for bringing the recorder into operation.

Figure 2:
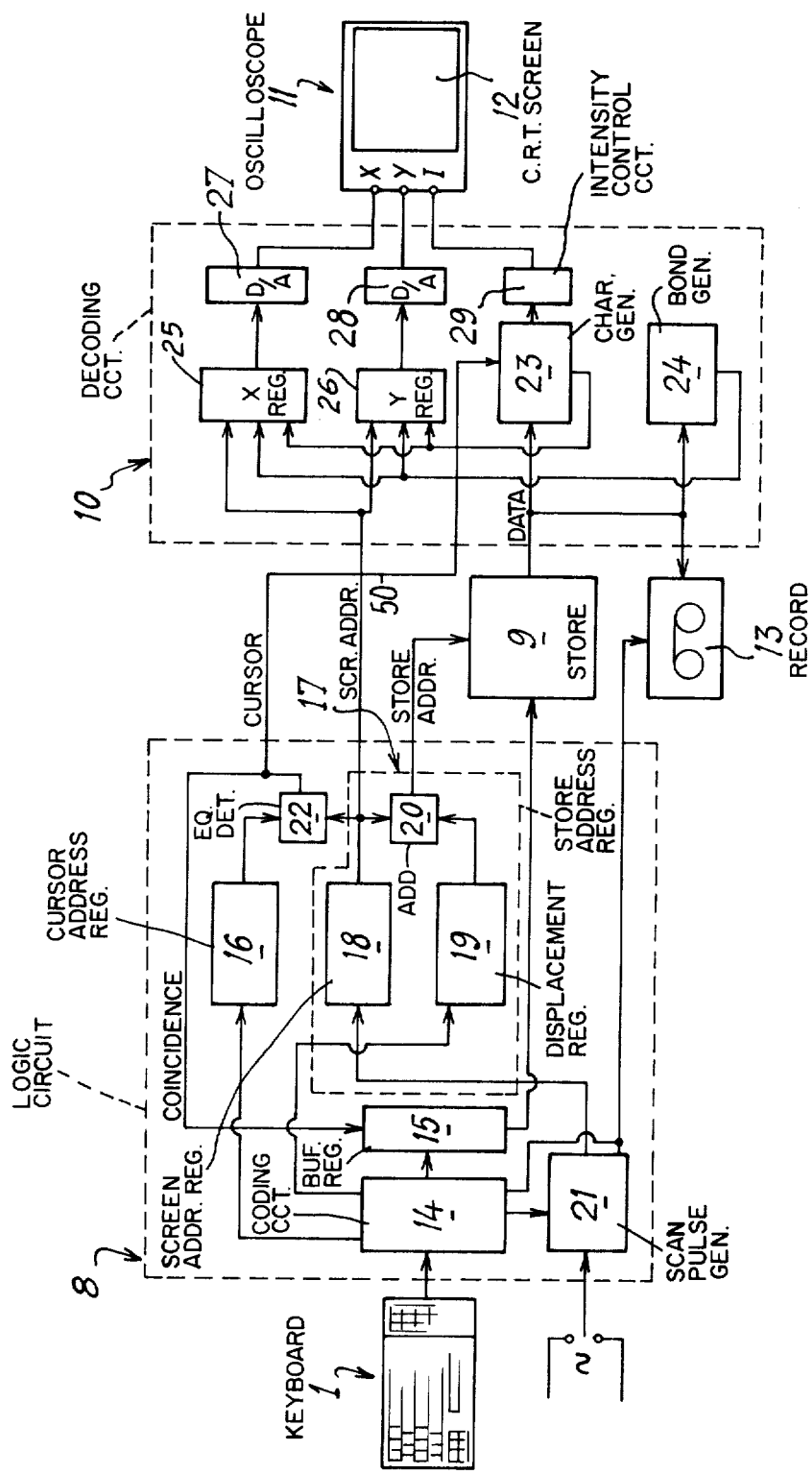
FIG. 2 is a more detailed block diagram of the functional diagram of FIG. 1.

The structure and operation of the various elements constituting the apparatus will now be described in more detailed fashion with reference to FIG. 2.

The logic circuit 8 comprises a coding circuit 14 which codes data provided by the keyboard. This data is of two types: graphical information and control information. In the class of graphical information, there are the alphanumeric characters representing the nodes or ring positions, the natures of the bonds and the directions of the bonds. The alphabetical characters are coded in the form of six-bit words in accordance with the six-bit code ASCII.

The acronym ASCII means American standard code for interchange of information and, accordingly, a wide variety of well-known devices are known for providing the standard six-bit code for alpha-numerical characters. The ASCII code covers not only the Latin alphabet and the Arabic digits, but various other symbols and functions also provided on typewriters or teletypewriters and of course some of these can be reassigned in the same way that typewriter keyboards are commonly rearranged. French Pat. Nos. 2,007,210, 2,138,053 and 2,232,972 illustrate the coding of keyboard actuations into distinctive multi-bit (sequential) codes.

The directions of the bonds, which are eight in number, can be coded in the form of three-bit words and the natures of the bonds can also be coded as three-bit words. These codes can be assigned in any pattern and the three-bit words are selected by the keys exactly as the ASCII six-bit words are selected. The control information is transcribed from the keying of control keys in the form of six-bit words, again in any assigned pattern. In order to differentiate the various graphical and control items of data, two supplementary code bits are added to each word and constitute the format thereof. Thus, the supplementary code 11 indicates an alphanumeric character, the codes 01 and 10 indicate the directions and types of bonds and the code 00 indicate control data. The graphical data, detected by the presence of a 1 in their supplementary code, are transmitted to a buffer register 15. The register 15 is designed and arranged to receive temporarily the coded graphical data relative to a node or ring position, that is to say either a code word representing the alphanumeric characters characterising this node or ring position or a code word representing the bonds extending from this node or ring position (these bonds being at most three in number). The typing of the graphical information on the keyboard is effected ring position by ring position, by successively striking (a) whatever alphanumeric character or characters which define the chemical symbol appearing at this ring position and the (b) directions and (c) natures of the bonds which extend from this ring position. The register 15 has a capacity of a six-bit word; each word so successively made is finally transferred to a location in the store 9 which, of course, is a random access memory (for example a 1K static RAM such as the 2102 of Intel or Signetics, the TMS4033 of Texas Instruments or the 91L02 of AMD).

A cursor address register 16 is linked to the keyboard through the coding circuit 14. The contents of the cursor address register 16 represent at any given moment the position of the cursor 30 at one of the finite number of points on the screen 12. Operation of the control key RC (cursor return) of the principal keyboard 1a positions the cursor 30 at a point of origin on the screen, for example half way up the screen 12 on the left-hand side, this being effected before starting the coding of a formula, bringing the cursor address register 16 to an initial condition. Since each point is defined by a row and column number, the cursor address register is of course made up of an $x$ counter and a $y$ counter, with provision for setting an initial condition. Counters are described at pages 254–265 of Digital Electronics for Scientists, by Malmstadt and Enke (M. A. Benjamin, Inc. 1969) for instance. The contents of the cursor address register 16, once set in the initial condition, are then modified (i.e. the $x$ or $y$ counters are stepped up or down) by any operation of a direction key 5 as a function of the direction indicated by this key, whether this operation is carried out for the coding of a bond or for positioning the cursor 30 at a point on the screen 12.

A store address register 17 is coupled to the store 9. The contents of this store address register 17 represent at any given moment the store location accessible at the input and at the output of the store 9. These contents are modified sequentially by the scanning pulse circuit 21, in such a manner as to effect a scanning of all the store locations sequentially at the scanning frequency. As mentioned before, there are typically 25 scan cycles per second (and the circuit 21 is coupled to the mains to set that rate, so that the pulses produced by the circuit 21 have a frequency in Hz, typically, of 25 times the number of locations on the screen 12; only the part of the store 9 corresponding to screen locations is, accordingly, scanned). Pulse generators for providing pulses of such a frequency in synchronism with the power mains frequency are well known and need not be further described. The scanning pulse circuit 21 is brought into operation from the keyboard 1 when the apparatus is started up, through the coding circuit 14.

Before the coding of a formula, the store can be cleared by operation of the key RZ (zero reset) of the principal keyboard 1a. Operation of the key RZ is interpreted by the coding circuit 14 which then commands the overall clearing of the store through a link not shown in FIG. 2. Before the commencement of the typing of a formula on the keyboard 1, the cursor 30 is positioned for example at the point of origin of the screen 12, as already mentioned, and the typing of the formula is initiated by typing successively, as has been described, all the graphical data, including the respective positions controlled by operation of keys 5, relating to the nodes or ring positions. These coded data are successively transmitted to the register 15 from which the data are transferred to the store 9 word by word when the contents of the cursor address register 16 and the store address register 17 coincide, and if the operator has actuated the control key M (memorisation or store) on the auxiliary keyboard. The coincidence of the contents of the cursor address register 16 and the store address register 17 is detected by the equality detector circuit 22 which provides at its output a signal authorising the transfer to the store 9 of any graphical data which may be contained in the register 15. Equality detectors are well known, being described for instance in the above cited Malmstadt and Enke text at pp. 177–8, and are available commercially in many bit capacities. Operation of the control key M is interpreted by the coding circuit 14 which controls, through a link not shown in FIG. 2, the entering into store of graphical data relating to a node or ring position available in the register 15. These graphical data thus occupy in the store a store location corresponding to the point of the screen 12 at which the cursor 30 is located. As the graphical data relating to a node or ring position are composed of six words at most, each store location is in fact composed of six sub-locations, three for alpha-numerical characters characterising the node or ring position and three for data relating to the bonds extending from this node or ring position.

The contents of a store location can be erased, for example in case of error, by operation of the control key EM (memory erase) of the principal keyboard 1a. To do this, the cursor 30 is positioned at the point of the screen at which the error appears and the key EM is operated, this key through the intermediary of the coding circuit 14 and the register 15 causing the erasure of the data in the store location at the address corresponding to that of the cursor address register 16.

As has been already mentioned above, the number of points on the screen may be less than the number of store locations. For this reason, the store address register 17 comprises a screen address register 18 and a displacement register 19. The content of the register 18 is, as above described, modified sequentially by the scanning pulse circuit 21 and is continuously added to that of the register 19, while their sum, obtained by means of a summing circuit 20, represents the store address at any given moment. The contents of the displacement register 19 can be modified by operation of a direction key 5 and operation of the control key D of the auxiliary keyboard, through the coding circuit 14. The screen address register 18, under the action of the scanning pulse circuit 21, as already mentioned, takes on successively and sequentially a number of different states equal to the number of points on the screen. The cursor address register 16 has the same number of possible different states and it is the contents of the screen address register 18 which are in fact compared by the equality detectors 22 with the contents of the cursor address register 16, to authorize the transfer into the store 9 of the data contained in the register 15 at the proper moment. A wide variety of adders are available commercially for adding binary numbers of various bit sizes. The proper size of be used for the circuit 20 depends upon the number of locations on the screen, of course. The various kinds of adders known, their manner of speed of operation, and their various input and output connections are described, for instance, in a publication identified as AN-35, entitled "High Speed TTL Adders," published by National Semiconductor Corp. in 1970, a six-page publication.

The decoding circuit 10 is connected to the output of the store 9, and it decodes the graphical data which are stored therein and which appear at the output in the sequence imposed by the scanning pulse circiut 21. The decoding circuit 10 comprises a character generator circuit 23 and a link or bond generator circuit 24. The character generator circuit 23, is of known type, and transcribes the coded alphanumeric data characterising the nodes or ring positions and is connected at its output to two registers, an abscissa register 25 and an ordinate register 26. These registers are advanced by the screen address register 18, which of course includes also a horizontal and a vertical counter, just as was explained above with regard to the cursor address register. The resisters 25 and 26 are connected at their outputs respectively to digital-analogue converter circuits 27 and 28, the outputs of which are respectively connected to the inputs of the X and Y time bases of the cathode ray oscilloscope 11.

The link or bond generator 24 similarly comprises, in a manner known in itself, two up-down counters which are connected respectively to the abscissa and ordinate registers 25 and 26 and to which are applied the data concerning the directions of the links or bonds. By modulating the intensity of the oscilloscope beam, by connections not shown but corresponding to those normally used in character generators, as a function of the data concerning the nature of the links or bonds, lines, points or dashes can be made to appear on the screen.

The link or bond generator 24 is just a simplified version of a character generator. In other words, instead of having to generate a display of any of the letters of the alphabet or any Arabic digit or possibly other signs, all it needs to show are lines, points or dashes, and the lines that need to be shown are either single, double or triple and have only eight possible directions from the node in question. This is a much simpler device than the conventional character generator that can display any alphabetic or numerical character. Consequently, the generation of any of these simple symbols in response to a six-bit word from the store 9 does not need to be described further here. An example of a vector generator, for showing vectors on the screen indicating speed and direction, and/or altitude and identify of aircraft disposed in a sector of space is disclosed in French Pat. No. 2,134,821, fully illustrating the generation of lines oriented in any direction at desired locations on a cathode ray tube.

The character generator circuit 23 has an intensity control circuit 29 that is provided not only to display the character being generated, but also to show the cursor on the screen. The intensity control circuit 29 has its output connected to the input I of the intensity control of the oscilloscope 11 and its input connected to control of the oscilloscope 11, to show the cursor on the screen. For this the character generator circuit 23 which is also connected to the equality detector circuit 22 by a connection 50 to generate the cursor display through the intermediary of the abscissa and ordinate registers 25 and 26 on one hand and the circuit 29 of the other when there is a coincidence between the contents of the cursor address register 16 and the screen address register 18.

The positioning on the screen 12 of the graphical data transcribed by the character generator 23 and the bond generator 24 is similarly effected by combining in the abscissa and ordinate registers 25 and 26 the graphical data and the state of the screen address register 18. To the extent that the number of alphanumeric characters defining a node or ring position can vary from one position to another, it is preferable to know this number in order to correctly position the characters with respect to the point on the screen at which this node or ring position must be located. For this purpose, to each coded alphanumeric character in a sub-location of a store location, there is added a supplementary code of two bits indicating the number of coded alphanumeric characters stored in this location. This supplementary code is interpreted in the abscissa and ordinate registers 25 and 26 in order to correctly place the first alphanumerical character characterising a node or ring position with respect to the point on the screen at which this node or ring position must be displayed. The store is thus constituted in such a manner as to contain eight-bit words in each sub-location.

Finally, it follows that the point on the screen corresponding to the state of the screen register does necessarily coincide with the origin of an alphabetical character from which the character generator 23 "effects" the outline of this character. Also, it is advantageous to "reframe" the data transcribed by the character generator 23 to obtain a very accurate positioning of the characters on the screen. The origin of a character, from which the character generator 23 effects the outline, is particular to each character and the "reframing" can be effected by means of a read-only memory, not shown in FIG. 2, located at the output of the character generator 23, so as to add its output algebraically to the character generator's counter output.

The "offset" read-only memory will of course respond to an address indicating whether the character is the first of three, the second of two, etc., and it can also serve to offset a bond in accordance with the direction part of the memory word.

There is shown in FIG. 4 a diagram such as might be displayed on the screen 12 with normal brilliance. The reference 31 indicates an extended simple bond. The coding and the display of such a bond are effected by actuating the control key C on the auxiliary keyborad, which serves to create a link extending a previously coded length. This can be obtained by coding by means of the key C, in the store location corresponding to the screen point which this extended link contains, a character which is other than alpha-numeric, to which is associated direction information, which is that of the extending link and information as to the nature of the extended link.

A line 32 is available for writing at the top or at the bottom of the screen. If data are to be coded and displayed on this line, this can be effected directly from the keyboard as for the coding and display of the graphical data. A control key EL (line erase) of the keyboard permits the erasing of information appearing in the line 32 and automatically positions the cursor at the beginning of this line. The alphanumeric data appearing in this line, associated with the graphical data shown on the screen, are available like the data relating to the graphical display for direct use in a computer.

As has been indicated above, a recording apparatus 13 connected to the output of the store 9 can record the coded formula with the object of subsequent data processing, for example to effect documentary research. Advantageously, this recording is effected on a data recording medium which can be directly used by a computer. The record medium contains coded data relating to the alphanumeric characters defining the nodes or ring positions and relating to the bond directions and natures, and also data relating to the extension links which are recognised by a coded character other than alphanumeric, and data relating to the line of writing. Although the number of characters at a node or ring position, according to the form described above, is limited to three, it is possible to record on the record medium data relating to a node or ring position comprising more than three characters. To do this, it suffices to introduce three characters successively into a store location, to record them, and to introduce in the same location the following characters and to record those conjointly with a coded order permitting the recognition, when the record medium is read, that these characters are all located at a single node or ring position. The apparatus can also be connected directly to peripheral equipment associted with a computer.

Although, according to the form of apparatus previously described, the number of characters at a single node or ring position is limited to three and the number of bonds extending from a single node or ring position is also limited to three, it will be evident that this limit of three is not essential and can be made larger by giving the circuits constituting the apparatus, and particularly the store, a greater capacity. The limit of three was in fact chosen because it is possible in such a case to represent graphically any structural chemical formula in a an unambiguous manner.

It will be noted that for simplicity a character defining a node or ring position need not be displayed or coded if this character occurs very frequently, as is the case in chemical formulae for the carbon atoms. The node or ring position occupied by this character will then be left blank.

The apparatus which has been described is particularly advantageous by reason of its simplicity of use and the high coding speed which can be obtained. Of course, it can be used for the coding of graphical data which does not necessarily represent chemical formulae.

The apparatus as previously described is an apparatus with a completely wired logic. However, it will be understood that certain functions, such as for example functions relating to coding, to the generation of the cursor, to storage, . . . , can be accomplished by means of micro-processors. In this case, such apparatus would here be called apparatus with partially wired logic. In any case, whether a particular function is effected by a micro-processor or by wired logic does not affect the autonomous character of the apparatus embodying the invention, which does not require, for its operation, control by a computer programmed for this purpose.

The micro-processors which can be used are small logical devices, the operation of which is governed by a micro-program written into a read-only memory. Operations which can be carried out by these micro-processors consist, for example, in the management of the "slow" inputs/outputs, that is to say the data coming from the keyboard and that intended for recording by the recorder 13 when the latter is, for example, a strip perforator or a printer.

On the other hand, in the case of "rapid" inputs/outputs, that is to say data coming from a magnetic recorder or intended for magnetic recording, the use of a micro-processor is not required and the access to the store is then direct.

We claim:

1. An apparatus for the simultaneous coding and display of structural chemical formulae and other graphical information composed of nodes or ring positions and links or bonds between these nodes, in which a node is identifiable by at least one alphanumeric character and a link is identifiable by graphical marking indicative of its nature and its direction, said apparatus comprising:

a keyboard including a first assembly of keys corresponding to different displayable alphanumeric characters, a second assembly of keys corresponding to displayable graphical marking indicative of a link and a third assembly of keys corresponding to different control functions for the apparatus;

a coding circuit for producing, in response to key actuation, signals of distinctive codes representative of the identity of the actuated key including as a part of each node a subcode identifying the one of said assemblies of which an actuated key is a member;

a store connected to said coding circuit for storing the signals produced by said coding circuit whenever they include a subcode identifying either said first or said second assembly of said keyboard, said store having a fixed number of addressable store locations in each of which said signals relating to a different node and to each link issuing therefrom is storable, one of said locations being available for each of a multiplicity of possible node or ring positions;

an oscilloscope having a screen comprising a fixed number of reference points and having an X-input, a Y-input and an intensity control input for displaying in graphical form data corresponding to said signals produced by said coding circuit, the positions of the nodes of said display data on the screen coinciding with locations of said points of the screen and the number of said points of the screen being less than the number of said addressable store locations of said store, whereby the matrix of points on the screen constitutes an image of a part of the matrix of store locations;

store address register means for cyclically addressing any collection of said store locations which can simultaneously correspond to the points on said screen of said oscilloscope and having an output connected to said store;

a scanning circuit connected to said store address register means for sequentially and cyclically varying the content thereof in such a way as to scan continuously the particular collection of store locations corresponding to said points on said screen at the time of scanning;

decoding means connected to said store for successively decoding the signals stored in said scanned store locations, said decoding means comprising an alphanumeric character generator and a graphical link generator connected to said inputs of said oscilloscope for producing a graphical display on the screen of said oscilloscope corresponding to the signals produced by said coding circuit in response to actuation of said keyboard;

shift control means connected to said store address register means and operable from said keyboard through said coding circuit for shifting the whole of the points on the screen relative to a corresponding array of the whole of the addressable store locations of said store, so as to change the collection of said addressable store locations which corresponds to the points on the screen;

means for generating an index cursor visible on said screen by affecting said intensity input of said oscilloscope;

means operable from said keyboard through said coding circuit for selectively positioning said cursor on said screen at a location thereof coinciding with a screen reference point, said cursor positioning means including a cursor address register connected to said coding circuit and having a content representative of the position selected for said cursor by operation of said keyboard, and an equality detector circuit connected to said store address register means and to said cursor address register for providing a storing authorization signal for selecting, for storage of signals from said coding circuit, the one of said addressable store locations in said store which corresponds to that of the cursor on the screen and for providing a command signal to said cursor generating means.

2. An apparatus as set forth in claim 1, wherein said store address register means comprises a screen address register and a displacement address register, said screen address register having a number of different possible states such that the number of different possible values of the sum of the contents of said screen address register and of said displacement address register is equal to the number of store locations, and an adding circuit having inputs respectively connected to said screen address register and to said displacement address register and an output constituting the output of said store address register means.

3. An apparatus as set forth in claim 2, wherein said cursor address register has a number of different possible states equal to the number of said reference points on the screen and said equality detector circuit compares the contents of said cursor address and screen address registers.

4. An apparatus as set forth in claim 1, wherein each of said addressable store locations of said store comprises a plurality of sub-locations for storing separately the signals corresponding to each of the alphanumeric characters and graphical markings relative to a node, and wherein said coding circuit is constituted so as to provide in response to operation of said keyboard, for the signals corresponding to each alphanumeric character relative to a node, a supplementary code indicating the number of alphanumeric characters identifying this node.

5. An apparatus as set forth in claim 1, wherein said decoding means comprises an abscissa register having an output connected to said X-input of the oscilloscope, and an ordinate register having an output connected to said Y-input of the oscilloscope, said abscissa and ordinate registers having inputs which are connected, on the one hand, to the alphanumeric character generator and to the graphical link generator of said decoding means and, on the other hand, to said address register means.

6. An apparatus as set forth in claim 5, and comprising first and second digital-analog converters serially connected respectively between said abscissa register and said oscilloscope X-input and betwen said ordinate register and said oscilloscope Y-input.

7. An apparatus as set forth in claim 1, wherein said scanning circuit is adapted to perform complete scans of a collection of locations of said store address register means corresponding to the points of said screen at a frequency at least equal to 15Hz.

* * * * *